(12) United States Patent
Keegan

(10) Patent No.: US 6,500,574 B2
(45) Date of Patent: Dec. 31, 2002

(54) METHOD AND APPARATUS FOR A FUEL CELL BASED FUEL SENSOR

(75) Inventor: Kevin R. Keegan, Hilton, NY (US)

(73) Assignee: Delphi Technologies, Inc., Troy, MI (US)

( * ) Notice: Subject to any disclaimer, the term of this patent is extended or adjusted under 35 U.S.C. 154(b) by 111 days.

(21) Appl. No.: 09/738,207

(22) Filed: Dec. 15, 2000

(65) Prior Publication Data
US 2002/0076590 A1 Jun. 20, 2002

(51) Int. Cl.$^7$ .............................. H01M 8/04; C25F 7/00
(52) U.S. Cl. .............................. 429/23; 429/30; 429/13; 204/228.1; 204/229.8
(58) Field of Search .............................. 429/23, 22, 13, 429/12, 30, 33; 204/421, 422, 424, 431, 196.02, 228.01, 229.8, 555, 556

(56) References Cited

U.S. PATENT DOCUMENTS

| 3,879,218 A | * | 4/1975 | Kellen et al. ................. 429/22 |
| 4,629,664 A | * | 12/1986 | Tsukui et al. ................. 429/23 |
| 5,478,662 A |   | 12/1995 | Strasser |

FOREIGN PATENT DOCUMENTS

| DE | 2146933 | 3/1973 |
| FR | 1486405 | 6/1967 |
| GB | 1148935 | 4/1969 |
| WO | 9741428 | 11/1997 |

OTHER PUBLICATIONS

Kim K–C et al; "Detection of ethanol gas concentration by fuel cell sensors fabricated using a solid polymer electrolyte" Sensors and Actuators B, Elsevier Sequoia S. A., Lausanne, vol. 67, No. 1–2; Aug. 10, 2000, pp. 194–198.
Mitura N et al: "High–temperature hydrogen sensor based on stabilized zirconia and a metal oxide electrode" Sensors and Actuators B, Elsevier Sequoia S.A., Lausanne, vol. 35, No. 1; Sep. 1, 1996, pp. 130–135.

* cited by examiner

*Primary Examiner*—Stephen Kalafut
*Assistant Examiner*—R Alejandro
(74) *Attorney, Agent, or Firm*—Vincent A. Cichosz

(57) ABSTRACT

Fuel concentrations are determinable in a solid oxide fuel cell through voltage measurement of one or more fuel cell units, which voltage is a function of hydrogen gas present in the fuel feed stream to the one or more fuel cell units. The voltage in the one or more fuel cell units is proportionally related to the fuel concentration in the fuel feed stream to the entire fuel cell. A sensor determines concentrations of the fuel flowing in the fuel cell. The sensor comprises a fuel cell unit, and an indicator electrically coupled to the fuel cell unit, the indicator being capable of displaying a voltage or being adapted to convert a voltage to a fuel concentration display. The voltage measured is correlated to the fuel concentration flowing in the fuel cell.

8 Claims, 1 Drawing Sheet

METHOD AND APPARATUS FOR A FUEL CELL BASED FUEL SENSOR

TECHNICAL FIELD

This disclosure relates to fuel cell systems and specifically to sensing a concentration of fuel within a fuel cell system.

BACKGROUND

A fuel cell is an energy conversion device that generates electrical energy and thermal energy by electrochemically combining a gaseous fuel and an oxidant gas across an ion conducting electrolyte. Several types of fuel cells currently exist. A characteristic difference between distinct types of fuel cell is the type of material used for the electrolyte. The difference in the materials of the electrolyte employed distinguishes the fuel cells due to the operating temperature ranges of the materials. In one type of fuel cell, the Solid Oxide Fuel Cell (SOFC), the fuel cell is constructed from solid-state materials utilizing an ion-conducting oxide ceramic as the electrolyte. To generate a useful quantity of power, a fuel cell is made up of multiple fuel cell units in a series array, typically stacked together. A single SOFC unit consists of two electrodes, one is an anode and one is a cathode. The anode and the cathode are separated by the solid electrolyte just identified. Fuel for the SOFC is typically gaseous hydrogen and carbon monoxide supplied in from reformats, and the oxidant is commonly an air supply. The fuel cell operates when the oxidant contacts the cathode and the fuel contacts the anode. The electrolyte conducts the oxygen ions between the cathode and the anode maintaining an overall electrical charge balance in the system. Electrons are released from the fuel cell to an external circuit forming a flow of electrons. The flow of electrons released from the fuel cell to the external circuit provides useful electrical power.

The production of useful electrical power is the primary function of the SOFC. Optimizing the conversion of fuel in the fuel cell is an endeavor that commands a significant amount of time and effort. As in many other energy conversion devices, the function of converting the fuel into useful energy, (electrical energy, thermal energy), is closely monitored by system operators. Quantifying the concentration of fuel flowing in the fuel cell provides a benefit during the operation of the fuel cell. The performance of the fuel cell is related to, and optimized by knowing the concentration of fuel being supplied to the fuel cell. Understanding the fuel concentration allows operators to understand what quantity of fuel to supply, and what electrical load to apply. Unfortunately, directly measuring the concentration of fuel such as hydrogen in the fuel cell creates many engineering challenges due to the limitations of hydrogen concentration sensors. The limitations of directly measuring hydrogen concentrations with sensors are amplified when applied to the SOFC, because the SOFC operates at high temperatures and uses high concentrations of hydrogen. The limitations are greatest with respect to sensing the concentration of hydrogen and the material compatibility of the sensor.

Direct measurement hydrogen concentration sensors are designed for concentrations that are very small compared to the relatively high SOFC hydrogen concentrations that exist during fuel cell operation. As a result, the direct measurement hydrogen concentration sensors are inadequate for use with solid oxide fuel cells.

In addition to the forgoing, existing hydrogen concentration sensors that measure hydrogen concentrations directly are not compatible with SOFC operating environments. Typically SOFC's exhibit high operating temperatures and a harsh environment both of which are detrimental to direct measurement hydrogen concentration sensors. Thus, there is a need in the art for a sensor that is compatible with both the operating environment and the relatively high levels of hydrogen concentration of the SOFC.

SUMMARY

Fuel concentrations are determinable in a solid oxide fuel cell through voltage measurement of one or more fuel cell units, which voltage is a function of hydrogen gas present in the fuel feed stream to the one or more fuel cell units. The voltage in the one or more fuel cell units is proportionally related to the fuel concentration in the fuel feed stream to the entire fuel cell. A sensor determines concentrations of the fuel flowing in the fuel cell. The sensor comprises a fuel cell unit, and an indicator electrically coupled to the fuel cell unit, the indicator being capable of displaying a voltage or being adapted to convert a voltage to a fuel concentration display. The voltage measured is correlated to the fuel concentration flowing in the fuel cell. The above described and other features and advantages of the present invention will be appreciated and understood by those skilled in the art from the following detailed description, drawings, and claims.

BRIEF DESCRIPTION OF THE DRAWINGS

The sensor will now be described, by way of an example, with references to the accompanying drawings, wherein like elements are numbered alike in the several figures.

DESCRIPTION OF THE PREFERRED EMBODIMENT

Figure 1:
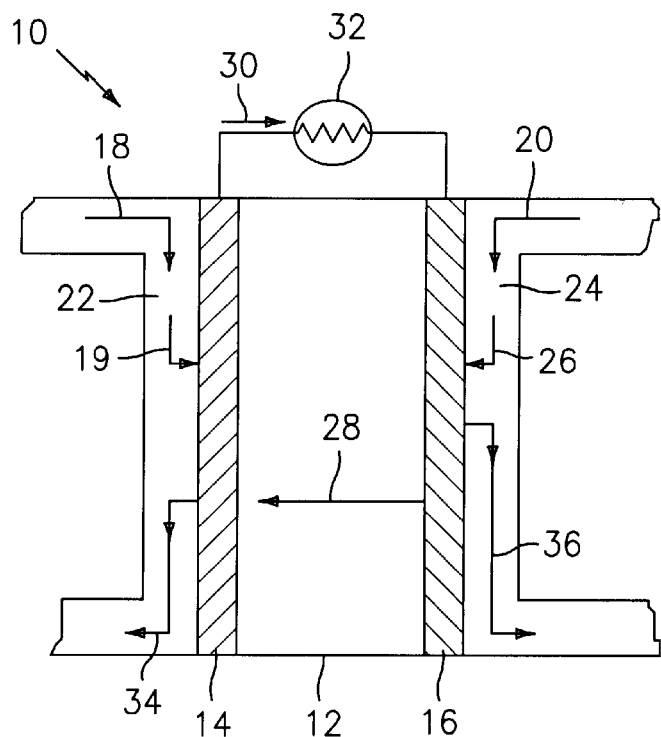
FIG. 1 is a schematic plan view of a fuel cell making up all or a part of a fuel cell.

Referring to FIG. 1, an exemplary embodiment of a fuel cell unit 10 is shown. In one embodiment, the fuel cell unit 10 is an assembly of an electrolyte 12, an anode 14 and a cathode 16, with the electrolyte 12 positioned between the anode 14 and the cathode 16 as illustrated. In a working fuel cell, one or more fuel cell units are employable. Typically more than one unit is employed to increase the total electrical energy output. In such multiple unit fuel cells, fuel cell unit 10 is repeated over and over to provide a serial assay of fuel cell units 10 to produce a desired quantity of electrical energy and thermal energy.

An understanding of the components of a solid oxide fuel cell and its operation will be helpful to understand this disclosure. The ceramic electrolyte 12, in one embodiment, is an yttria-stabilized-zirconia (YSZ). This ceramic electrolyte 12 exhibits good oxygen ionic conductivity and little electrical conductivity at high temperatures (700–1000 degrees centigrade). The electrodes, in one embodiment, are porous, gas-diffusion electrodes. The anode 14 is about 20–40 percent porous and is formed from a metallic nickel and an YSZ skeleton for thermal compatibility with the other components. The cathode 16 is made from strontium-doped lanthanum manganite with about the same porosity as the above embodiment of the anode 14. In other embodiments the materials may vary. Because the fuel cell is solid state, the thermal expansion coefficients of as many as four different ceramic layers must be well matched in the fuel cell unit 10. A high operating cell temperature in the SOFC is required to maximize the ionic conductivity of the electrolyte and ensure good electrical conductivity of the electrodes and interconnections. As a result, the critical cell components are made from various ceramics, metal-ceramic composites, and high temperature alloys that are compatible with the operating environment of the SOFC.

The fuel cell unit 10 may be configured in a variety of geometries including tubular planar stack and radial planar geometries. The fundamental electrochemical processes of the fuel cell unit 10 remain the same for various cell geometries. In the embodiment shown in FIG. 1, during operation, fuel 18, (typically reformate containing hydrogen reformed from diesel fuel, gasoline, natural gas, propane, or methanol), flows through channel 22 and oxidant 20, typically air, flows through channel 24, respectively. Each electrode, (cathode 16, anode 14), is exposed to the reactant gases 20, 18. The anode 14 is exposed to or contacted with the fuel 18 and the cathode 16 is exposed to or contacted with the oxidant 20. More specifically, the fuel cell unit 10 operates when the oxidant 20 having oxygen ions 26, contacts the cathode 16, where the oxygen ions 26 are adsorbed by the cathode 16. The oxygen ions 26 diffuse to the cathode-electrolyte interface and are reduced, (gains electrons). The mobile ionic species are negatively charged oxygen ions. Continuing with the fuel cell operation, negative ions (anions) 28 migrate across the electrolyte 12. The migrating anions 28 carry the negative charge to the electrolyte-anode interface. At the anode 14, hydrogen 19 is oxidized. Because of hydrogen's affinity for oxygen, the hydrogen 19 flowing past the anode 14 is adsorbed by the anode 14, where the hydrogen diffuses through the porous anode 14 to the anode-electrolyte interface, where as mentioned above, the hydrogen 19 is oxidized (loses electrons). The fuel cell unit 10 creates a flow of electrons 30 (electron flow). The flow of electrons 30 is conducted to an electrical load 32 via an electrical circuit (not shown). The electrical circuit maintains the flow of electrons 30 from the anode 14 to the electrical load 32 and continues to the cathode 16. The electron flow 30 flows from the negative charge at the anode 14 to the positive charge at the cathode 16. The electrical current (not shown), flows opposite the electron flow 30 from a high electrical potential at the cathode 16 to a low electrical potential at the anode 14. In addition to electron flow 30, the fuel cell produces reaction products from both electrodes while in operation. The anode reaction products 34 (product gases and depleted fuel, or combustion products) of the fuel cell unit 10 are typically water, carbon dioxide, hydrogen, carbon monoxide and other products, depending on the fuel 18. Thermal energy is also a discharged product 34. Cathode reaction products 36 (excess or depleted oxidant and product gases), typically air and water are also discharged. As stated previously, the fuel cell unit 10, including the electrolyte 12 disposed between the anode 14 and the cathode 16 produces a limited quantity of electrical energy and thermal energy. Combining an individual fuel cell unit 10 with multiple fuel cell units 10 otherwise known as stacking, increases generating capacity amounting to a quantity of useful electrical and thermal energy. The serial array of individual fuel cell units 10, creates a complete fuel cell, (sometimes known as a fuel cell stack; not shown).

The electrochemical processes that occur in the fuel cell unit 10 can be related to the electrochemical processes that occur in the entire fuel cell. The flow of electrons 30 from the fuel cell unit 10 is related to the sum of all electrons flowing 30 through the entire fuel cell. The electrons flowing 30 through the fuel cell are related to an electrical potential of fuel cell. Electrical potential is measured as voltage. The voltage of the fuel cell is a strong function of the concentration of the hydrogen 19 (fuel 18) in the feed stream of fuel of fuel cell. Likewise, the voltage of the fuel cell unit 10 is a strong function of the concentration of the hydrogen 19 (fuel 18) in the feed stream of fuel to the fuel cell unit 10. Stated another way, the concentration of the hydrogen in the fuel cell is related to the flow of electrons 30 and to the electrical load 32. The operability of the fuel cell is related to the concentration of fuel 18 in the fuel cell. Throughout the operation of the fuel cell, the concentration of fuel 18, is a parameter that indicates SOFC system performance. In a preferred embodiment, the concentration of hydrogen is a parameter that is used to optimize the performance of the fuel cell. More specifically, the knowledge of the concentration of the hydrogen in the fuel stream being presented to the stack of fuel cell units 10 is a parameter that can be used to optimize the performance of the system. It has been determined by the inventors herein that measured voltage of one or more fuel cell units can be repeatably and reliably correlated to a concentration of reformate flowing in the fuel stream to the fuel cell. The relationship of the flow of electrons 30 to the concentration of hydrogen 19 allows for measurement of the concentration of hydrogen 19 indirectly by measuring the voltage of one or more fuel cell unit(s) 10. The voltage measurement of even a single fuel cell is correlatable to the reformate concentration in the entire fuel cell.

Figure 2:
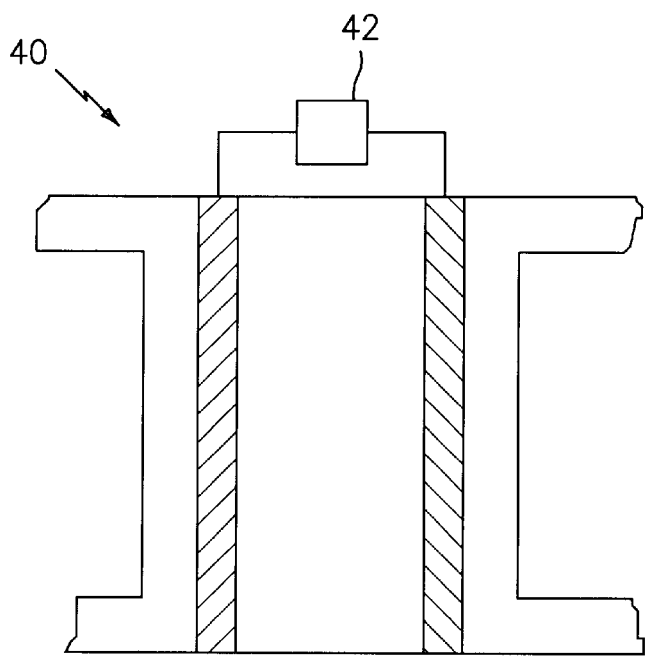
FIG. 2 is a schematic plan view of an exemplary embodiment of a fuel cell unit based sensor.

Turning now to FIG. 2, an exemplary embodiment of a fuel cell based fuel concentration sensor 40, hereinafter, sensor 40, is shown. The fundamental electrochemical processes of the sensor 40 remains the same as the electrochemical processes of the fuel cell unit 10 regardless of the various cell geometries. FIG. 2, illustrates an arrangement of a preferred embodiment of a sensor 40 that directly measures the voltage of the fuel cell unit 10 and indirectly allows determination of the concentration of hydrogen in the fuel cell. The sensor 40 has the same basic components and materials as the fuel cell unit 10 shown in FIG. 1, with the substitution of the electrical load 32 for an indicator 42. The indicator 42 measures and indicates the voltage of the sensor 40. The components of an individual fuel cell unit 10 or, in one embodiment, a portion of the fuel cell unit 10 is utilized as the sensor 40. The sensor 40 is nestable with the fuel cell. In an embodiment, multiple sensors 40 are disposed or nested within the fuel cell. Sensors 40 can be intermittently disposed throughout the fuel cell stack to provide an array of indications within the cell geometry. In certain fuel cell geometries, the fuel cell units 10 may experience different operating conditions at different locations within the fuel cell, so placement of individual sensors 40 in different locations within the stack is also contemplated. In the preferred embodiment, the sensor 40 is not electrically connected to other fuel cell units 10 in the stack of the fuel cell. The sensor 40 is isolatable from the fuel cell stack. The sensor 40 is not connected to the electrical load 32.

The sensor 40 has the material properties to function in the environment of the fuel cell unit 10. A hydrogen concentration sensor made from the same materials as the fuel cell components can withstand the SOFC operating environment. In a preferred embodiment, the sensor 40 has the same electrolyte 12 materials, the same anode 14 materials and the same cathode 16 materials as an individual fuel cell unit 10. The sensor 40 is capable of determining the high concentrations of fuel that are encountered in the fuel cell unit 10. The capability to determine the relatively high concentrations is due to the proportional relationship of the voltage and the fuel concentration in the fuel cell unit 10. In a preferred embodiment, the sensor 40 is compatible with the SOFC using hydrogen as a fuel, where the hydrogen has a wide range of concentrations. A hydrogen concentration sensor that is not limited to relatively small hydrogen concentrations can measure hydrogen concentrations within the SOFC.

Measuring the voltage with the sensor 40 provides data which is correlatable to the hydrogen concentration in the fuel cell because the voltage of the sensor is proportional to the concentration of hydrogen being presented to the fuel cell. The indicator 42, in one embodiment, can be used simply to provide the data taken from measuring the voltage. The data can then be used to correlate the voltage to the hydrogen concentration. In another embodiment, the indicator 42 can measure the voltage and correlate the data taken from the measurement into a hydrogen concentration in a display. Measuring the voltage of the sensor 40 enables monitoring hydrogen 19 concentrations or other fuel 18 concentrations in other embodiments.

A comparison of the voltage measured in the electrically isolated sensor 40 to the total voltage of the electrically loaded fuel cell units 10 stacked in the fuel cell is also considered in an alternate embodiment. A variety of fuel cell performance characteristics can be assessed, such as contamination within the fuel cell unit 10, aging, and fuel cell efficiency, by knowing the concentration of hydrogen in the fuel cell. The fuel cell unit 10 fuel flow rates as well as electrical load 32 can be controlled more efficiently as a result of having the capability to detect the voltage of the sensor 40 and correlate a fuel concentration in the fuel cell. It is contemplated that applying varying electrical loads 32 to the sensor 40 and measuring the output impedance of the sensor 40 thus determining a relationship of the concentration of reformate (fuel 18) with the output impedance of the sensor 40.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the claims.

What is claimed is:

1. A method of sensing a fuel concentration of a fuel cell comprising:

measuring a voltage of said fuel cell, wherein said fuel cell is a solid oxide fuel cell; and determining said fuel concentration flowing through said fuel cell based on said voltage.

2. The method of sensing a fuel concentration of a fuel cell as in claim 1 wherein said determining comprises:

correlating said voltage to said fuel concentration.

3. The method of sensing a fuel concentration of a fuel cell as in claim 2 wherein said measuring is done with at least a portion of at least one sensor, said at least one sensor includes;

a cathode;

an anode spaced from said cathode; and an electrolyte disposed between said cathode and said anode; and an indicator electrically coupled to both said anode and said cathode.

4. The method of sensing a fuel concentration of a fuel cell as in claim 3 wherein said indicator determines said voltage of said at least one sensor.

5. The method of sensing a fuel concentration of a fuel cell as in claim 2 wherein said fuel cell has a plurality of fuel cell units, each of said plurality of fuel cell units include;

a cathode;

an anode spaced from said cathode; and an electrolyte disposed between said cathode and said anode;

a fuel flow contacting said anode;

an oxidant flow contacting said cathode;

an electron flow of said fuel cell unit coupled from said anode to an electrical load and said electrical load coupled to said cathode wherein said electron flow of said plurality of fuel cell units flows through said anode, to said electrical load, to said cathode.

6. The method of sensing a fuel concentration of a fuel cell as in claim 3 wherein said at least one sensor in said fuel cell is electrically isolated from an electron flow of said fuel cell.

7. The method of sensing a fuel concentration of a fuel cell as in claim 5 wherein said fuel flow is hydrogen; and said oxidant flow is air.

8. The method of sensing a fuel concentration of a fuel cell as in claim 5 wherein said correlating said voltage to said fuel concentration comprises varying said electrical load, measuring said voltage at said sensor, and relating said voltage to said fuel concentration with respect to said varying electrical load.

* * * * *